(12) United States Patent
Hermeling et al.

(10) Patent No.: US 7,652,111 B2
(45) Date of Patent: Jan. 26, 2010

(54) (METH)ACRYLIC ACID ESTERS OF UNSATURATED AMINOALCOHOLS AND PREPARATION THEREOF

(75) Inventors: Dieter Hermeling, Böhl-Iggelheim (DE); Thomas Daniel, Waldsee (DE); Mark Elliott, Ludwigshafen (DE); Ulrich Riegel, Landstuhl (DE); Frank Dietsche, Schriesheim (DE); Reinhold Schwalm, Wachenhaim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 618 days.

(21) Appl. No.: 10/576,892

(22) PCT Filed: Nov. 18, 2004

(86) PCT No.: PCT/EP2004/013064

§ 371 (c)(1),
(2), (4) Date: Apr. 24, 2006

(87) PCT Pub. No.: WO2005/058987

PCT Pub. Date: Jun. 30, 2005

(65) Prior Publication Data

US 2007/0043191 A1  Feb. 22, 2007

(30) Foreign Application Priority Data

Nov. 25, 2003  (DE) ................................ 103 55 401

(51) Int. Cl.
*C08F 118/02* (2006.01)
*C07C 229/02* (2006.01)
(52) U.S. Cl. ...................................... 526/319; 560/222
(58) Field of Classification Search ................. 526/319; 560/222
See application file for complete search history.

(56) References Cited

U.S. PATENT DOCUMENTS

| 4,796,427 | A |  | 1/1989 | Zeyher |
| 4,897,220 | A |  | 1/1990 | Trieselt et al. |
| 5,104,951 | A |  | 4/1992 | Seelmann-Eggebert et al. |
| 5,478,883 | A | * | 12/1995 | Anchor et al. ............... 524/812 |
| 5,837,789 | A |  | 11/1998 | Stockhausen et al. |
| 6,268,521 | B1 | * | 7/2001 | Gruning et al. ............. 560/209 |
| 6,710,141 | B1 |  | 3/2004 | Heide et al. |
| 2003/0091602 | A1 | * | 5/2003 | Witteler et al. ............. 424/401 |
| 2003/0143908 | A1 | * | 7/2003 | Andre et al. ................ 442/118 |
| 2004/0014901 | A1 |  | 1/2004 | Heide et al. |
| 2004/0186229 | A1 |  | 9/2004 | Heide et al. |
| 2006/0235141 | A1 |  | 10/2006 | Riegel et al. |

FOREIGN PATENT DOCUMENTS

| DE | 37 16 543 | 11/1988 |
| DE | 38 18 426 | 12/1989 |
| DE | 196 46 484 | 5/1997 |
| DE | 199 55 861 | 5/2001 |
| DE | 103 58 372 | 10/2004 |
| EP | 0 223 063 | 5/1987 |
| WO | WO-90/15830 | 12/1990 |
| WO | WO-02/32964 | 4/2002 |

OTHER PUBLICATIONS

International Search Report for PCT/EP2004/013064 dated Feb. 25, 2005.

* cited by examiner

*Primary Examiner*—David Wu
*Assistant Examiner*—Michael M Bernshteyn
(74) *Attorney, Agent, or Firm*—Marshall, Gerstein & Borun LLP

(57) ABSTRACT

Disclosed are novel (meth)acrylic esters of unsaturated amino alcohols, a process for their preparation and their use for preparing crosslinked swellable hydrogel-forming polymers and crosslinked swellable hydrogel-forming polymers.

17 Claims, No Drawings

(METH)ACRYLIC ACID ESTERS OF UNSATURATED AMINOALCOHOLS AND PREPARATION THEREOF

CROSS-REFERENCE TO RELATED APPLICATIONS

This is the U.S. national phase application of International Application No. PCT/EP2004/013064, filed Nov. 18, 2004, which claims the benefit of German patent application No. 103 55 401.7, filed Nov. 25, 2003.

The present invention relates to (meth)acrylic esters of unsaturated amino alcohols, a process for their preparation and also their use for preparing crosslinked swellable hydrogel-forming polymers and crosslinked swellable hydrogel-forming polymers.

The terms (meth)acrylic acid and (meth)acrylic ester as used herein represent methyacrylic acid and acrylic acid on the one hand and methacrylic ester and acrylic ester on the other.

Swellable hydrogel-forming polymers, known as superabsorbent polymers or SAPs, are known from the prior art. They are networks of flexible hydrophilic polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed, for example for storage, packaging, transportation, in medicine and in cosmetics.

Hydrophilic high-swell hydrogels are in particular polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products which swell in aqueous fluids, for example guar derivatives. Such hydrogels are used as products which absorb aqueous solutions to manufacture diapers, tampons, sanitary napkins and other hygiene articles, but also as water-retaining agents in market gardening.

Good transportation properties are possessed for example by hydrogels having high gel strength in the swollen state. Gels lacking in strength are deformable under an applied pressure, for example pressure due to bodyweight, and clog the pores in the SAP/cellulose fiber absorbent and so prevent continued absorption of fluid. Enhanced gel strength is generally obtained through a higher degree of crosslinking, although this reduces retention performance of the product. An elegant way to enhance gel strength is surface postcrosslinking. In this process, dried superabsorbents having an average crosslink density are subjected to an additional crosslinking step. Surface postcrosslinking increases the crosslink density in the surface shell of the superabsorbent particle, whereby the absorbency under load is raised to a higher level. Whereas the absorption capacity decreases in the superabsorbent particle shell, the core has an improved absorption capacity (compared to the shell) owing to the presence of mobile polymer chains, so that shell construction ensures improved fluid transmission without occurrence of the gel blocking effect. It is perfectly desirable for the total capacity of the superabsorbent to be exhausted not spontaneously but with time delay. Since the hygiene article is generally repeatedly insulted with urine, the absorption capacity of the superabsorbent should sensibly not be exhausted after the first disposition.

DE-A-196 46 484 describes fluid-absorbing polymers which are preparable using a crosslinker-monomer combination consisting of three components, the first component being a compound having a (meth)allyl and a (meth)acrylic ester function, the second component being mono(meth)acrylic esters or mono)(meth)allyl alcohol ethers of polyalkylene glycols and the third component being esters of unsaturated acids with polyols or di- or triallylamine or bisacrylamides.

WO 90/15830 discloses a water-swellable hydrocolloid polymer which contains a copolymerized crosslinker mixture which comprises a bis- or trisacyloyl-containing first crosslinker and a second crosslinker selected from bisallyl ethers, bisallyl amides, bisallylamines and triallylamine.

WO 02/32964 recommends a crosslinker mixture composed of a first crosslinker having at least two (meth)acrylic ester units per molecule and a second crosslinker having at least two (meth)allyloxy units per molecule for preparing crosslinked, water-swellable polymers.

Water-swellable addition polymers are economically producible in a continuous process. For instance, EP-A-0 223 063 teaches a process for continuous production of crosslinked fine particles of addition polymers in gel form in a single-screw cylindrical mixer whose mixing segments are effective to convey the materials from the upstream end to the downstream end of the cylindrical mixer.

DE-A-199 55 861 describes a process for continuous production of crosslinked fine particles of addition polymers in gel form wherein an aqueous solution of water-soluble monoethylenically unsaturated monomers and crosslinkers is fed to a specially constructed mixing kneader.

It is an object of the present invention to provide crosslinked water-swellable polymers having a balanced property profile with regard to absorption capacity, gel strength, takeup rate and extractables that are also advantageously producible in a continuous process.

Triallylamine internal crosslinker provides water-swellable polymers having low extractables, especially when the polymerization is carried out in a neutral or basic medium. But there is a disadvantage with the use of triallylamine in that triallylamine and the impurities present in triallylamine (monoallylamine and diallylamine) have toxic properties. Moreover, allylamines are quickly absorbed through the skin and are volatile (monoallylamine boiling point 58° C., diallylamine boiling point 111° C., triallylamine boiling point 155° C.).

There accordingly continued to be need for internal crosslinkers which make it possible to produce water-swellable polymers having a low extractables fraction and which are less toxic and less volatile than triallylamine.

Unless otherwise mentioned, crosslinking as used herein is to be understood as meaning gel crosslinking, internal crosslinking or cross-linking of linear or lightly crosslinked polymer. This crosslinking can take place via free-radical or cationic polymerization mechanisms or other mechanisms, for example Michael addition, esterification or transesterification mechanisms, but is preferably effected by free-radical polymerization.

Crosslinked swellable hydrogel-forming polymers are preferably capable of absorbing at least 10 times their own weight and preferably 20 times their own weight, based on the polymer used, of 0.9% by weight sodium chloride solution. This absorption is preferably achieved even under a pressure of for example 0.7 psi.

We have found that the aforementioned objects are achieved by using novel crosslinkers.

The present invention accordingly provides (meth)acrylic esters of unsaturated amino alcohols of the general formula I

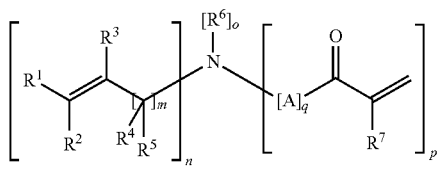
(I)

where $R^1$, $R^2$, $R^3$, $R^4$ and $R^5$ are each independently hydrogen or $C_1$ to $C_6$ alkyl, of which $C_3$ to $C_6$ alkyl may be branched or unbranched, $R^6$ $C_1$ to $C_6$ alkyl, of which $C_3$ to $C_6$ alkyl may be branched or unbranched, $R^7$ is hydrogen or methyl, m is an integer from 0 to 10, n is 1 or 2, o is 0 or 1, p is 1 or 2, q is an integer from 2 to 100, the sum total of n, o and p is 3, and A represents identical or different radicals selected from the group consisting of

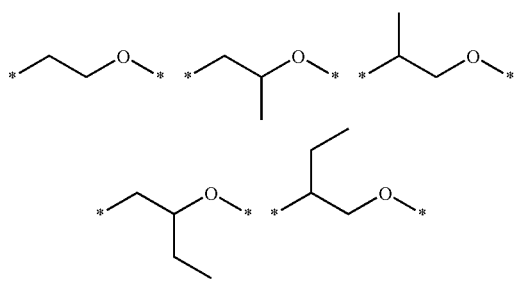

where * identifies the positions of attachment.

Preference is given to (meth)acrylic esters of unsaturated amino alcohols of the general formula I, where $R^1$, $R^2$, $R^3$, $R^4$ and $R^5$ are each hydrogen, $R^6$ $C_1$ to $C_3$ alkyl, of which $C_3$ alkyl may be branched or unbranched, $R^7$ is hydrogen or methyl, m is 0 or 1, n is 1 or 2, o is 0 or 1, p is 1 or 2, q is an integer from 3 to 40, the sum total of n, o and p is 3, and A represents identical or different radicals selected from the group consisting of

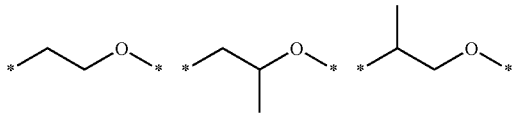

where * identifies the positions of attachment.

Particular preference is given to (meth)acrylic esters of unsaturated amino alcohols of the general formula I, where $R^1$, $R^2$, $R^3$, $R^4$ and $R^5$ are each hydrogen, $R^7$ is hydrogen or methyl, m is 1, n is 1 or 2, o is 0, p is 1 or 2, q is an integer from 5 to 20, the sum total of n, o and p is 3, and A is

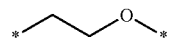

where * identifies the positions of attachment.

The inventive (meth)acrylic esters of unsaturated amino alcohols are preparable for example from an alcohol of the general formula II

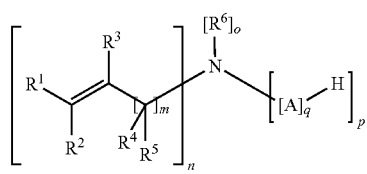
(II)

where $R^1$, $R^2$, $R^3$, $R^4$, $R^5$, $R^6$, m, n, o, p, q and A are each as defined above, by transesterification with (meth)acrylic esters and also by acidolysis with (meth)acryloyl chloride or (meth)acrylic anhydride. Transesterification with lower (meth)acrylic esters is preferred. Lower (meth)acrylic esters are (meth)acrylic esters having a lower boiling point than the target ester.

Such transesterifications can be prepared for example enzymatically, as described for example in EP-A-0 999 229, or under base catalysis, as described for example in GB-1,112,439.

Useful unsaturated amino alcohols include alkoxylated unsaturated amines which are obtainable by reaction of an unsaturated amine with at least one alkylene oxide.

Suitable unsaturated amines are for example diallylamine, allylamine, methylallylamine, ethylallylamine, propylallylamine, divinylamine, vinylamine, methylvinylamine, ethylvinylamine and propylvinylamine. Diallylamine, allylamine and methylallylamine are preferred and diallylamine is very particularly preferred.

Useful alkylene oxides include for example ethylene oxide, propylene oxide and/or butylene oxide.

The alkylene oxide chain may preferably be composed of ethylene oxide, propylene oxide and/or butylene oxide units. Such a chain can be composed of one species of an alkylene oxide or of a mixture of alkylene oxides. When a mixture is used, the different alkylene oxide units may be present randomly or as a block or blocks of individual species. The alkylene oxide is preferably ethylene oxide, propylene oxide or a mixture thereof, more preferably ethylene oxide or a mixture of ethylene oxide and propylene oxide are most preferably ethylene oxide.

The preferred number of alkylene oxide units in each chain is dependent on the number of chains and is for p=2 in the range from 2 to 100, preferably from 3 to 30, more preferably from 5 to 15 and for p=1 in the range from 2 to 100, preferably from 5 to 40, more preferably from 8 to 20 alkylene oxide units in every chain.

The stated degrees of alkoxylation each relate to the average degree of alkoxylation.

It will be appreciated that the process of production will generally give rise to mixtures in which lower and higher oligomers may be present in addition.

The reaction of unsaturated amines with an alkylene oxide is known per se to one skilled in the art. Possible ways of conducting the reaction may be found in HoubenWeyl, Methoden der Organischen Chemie, 4$^{th}$ edition, 1963, Thieme Verlag Stuttgart, volume 14/2, pages 440 to 444.

With mixed-alkoxylated unsaturated amines are used, the different alkoxy groups present therein may be in a molar ratio to each other which is for example 0.05-20:1, preferably 0.1-10:1 and more preferably 0.2-5:1

The viscosity of the unsaturated amines which can be used according to the present invention is not subject to any particular requirements bar that they should be readily pumpable to about 80° C., preferably they should have a viscosity below 1000 mPas, preferably below 800 mPas and most preferably below 500 mPas.

Useful meth(acrylic) esters for the invention are for example methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, 2-ethylhexyl acrylate and 2-ethylhexyl methacrylate, preferably methyl acrylate, ethyl acrylate and n-butyl acrylate.

Useful transesterification catalysts include in particular titanium, alkoxides whose alkyl groups are $C_1$-$C_4$-alkyl radicals, for example tetramethyl, tetraethyl, tetraisopropyl, tetra-n-propyl, tetraisobutyl and tetra-n-butyl titanate (see for example EP-B-0 298 867, EP-A-0 960 877). Useful catalysts further include titanium phenoxides (DE-A-20 08 618), metal chelate compounds of for example hafnium, titanium, zirconium or calcium, alkali metal and magnesium alkoxides, organic tin compounds or calcium and titanium compounds, for example oxides, hydroxides, carbonates or halides. Useful transesterification catalysts further include strongly basic ion exchangers or zeolites. Preference is given to titanium alkoxides and sodium alkoxides. Very particular preference is given to titanium alkoxides and sodium alkoxides whose alcohol component corresponds to the alcohol component of the lower (meth)acrylic ester used.

Since, as will be known, a transesterification is an equilibrium reaction, one of the starting materials is used in large excess and/or one of the reaction products is removed from the equilibrium in order that commercial conversions may be achieved. The lower alcohol released in the course of the transesterification is therefore typically removed from the equilibrium by distillation. The disadvantage with this is that the released alcohols, typically methanol, ethanol or n-butanol, combine with the corresponding (meth)acrylic esters (methyl acrylate, ethyl acrylate and n-butyl acrylate respectively) to form an azeotrope and thus are not directly separable by distillation.

It is ecologically and economically advantageous to recycle the distilled-off mixture or azeotrope or its individual components (alcohol and/or (meth)acrylic ester) into the production of the (meth)acrylic ester (for example methyl acrylate, ethyl acrylate or n-butyl acrylate).

Useful polymerization inhibitors include for example phenols such as alkylphenols, for example o-, m- or p-cresol (methylphenol), 2-tert-butyl-4-methylphenol, 2,6-di-tert-butyl-4-methylphenol, 2-tert-butylphenol, 4-tert-butylphenol, 2,4-di-tert-butylphenol, hydroquinone, pyrocatechol (1,2-dihydroxybenzene), aminophenols, for example paraaminophenol, nitrosophenols, for example para-nitrosophenol, p-nitroso-o-cresol, alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), tocopherols, for example, α-tocopherol, β-tocopherol, γ-tocopherol, β-tocopherol and ε-tocopherol, tocol, α-tocopherolhydrochinone, quinones and hydroquinones, for example hydroquinone or hydroquinone monomethyl ether, 2,5-di-tert.-butylhydroquinone, benzochinone, diphenylethene, N-oxyls, for example 4-hydroxy-2,2,6,6-tetramethylpiperidine-N-oxyl, 4-oxo-2,2,6,6-tetramethylpiperidine N-oxyl, 4-acetoxy-2,2,6,6-tetramethylpiperidine-N-oxyl, 2,2,6,6-tetramethylpiperidine N-oxyl, aromatic amines, for example phenylendiamines, N,N-diphenylamine, N-nitrosodiphenylamine, nitrosodiethylaniline, N,N'-dialkylpara-phenylendiamine, wherein the alkyl radicals may be identical or different and may each independently consist of 1 to 4 carbon atoms and be straight-chain or branched, for example N,N'-diisobutyl-pphenylendiamine, N,N'-di-iso-propyl-p-phenylendiamine, hydroxylamines, for example N,N-diethylhydroxylamine, urea derivatives, for example urea or thiourea, phosphorus compounds, for example, triphenylphosphine, triphenyl phosphite, hypophosphorous acid or triethyl phosphite, sulfur compounds, for example diphenyl sulfide, phenothiazine or metal salts, for example copper chloride, copper dithiocarbamate, copper sulfate, copper salicylate, copper acetate, manganese chloride, manganese dithiocarbamate, manganese sulfate, manganese salicylate, manganese acetate, cerium chloride, cerium dthiocarbamate, cerium sulfate, cerium saslicylate, cerium acetate, nickel chloride, nickel dithiocarbamate, nickel sulfate, nickel salicylate, nickel acetate, chromium chloride, chromium dithiocarbamate, chromium sulfate, chromium salicylate, chromium acetate or mixtures thereof.

Preference is given to the phenols and quinones mentioned and particular preference is given to hydroquinone, hydroquinone monomethyl ether, 2-tert-butyl-4-methylphenol, 2,6-di-tert-butyl-4-methylphenol, 2,4-di-tert-butylphenol, α-tocopherol, diphenylethene, triphenyl phosphite, hypophosphorous acid, $CuCl_2$ and guaiacol.

Particular preference is given to hydroquinone monomethyl ether, α-tocopherol, hydroquinone and alkylphenols, diphenylethene, optionally in combination with triphenyl phosphite and/or hypophosphorous acid.

Very particular preference is given to hydroquinone monomethyl ether, α-tocopherol, diphenylethene or mixtures thereof.

Stabilization may be further augmented by the presence of an oxygen-containing gas, preferably air or a mixture of air and nitrogen (lean air). The oxygen-containing gas more preferably contains less than 10% by volume of oxygen and most preferably from 4 to 6% by volume of oxygen.

Among the recited stabilizers, preference is given to those which are aerobic, i.e., those which required the presence of oxygen to fully develop their inhibiting effect.

The transesterification may of course also be carried out using solvents, particularly solvents which are suitable for axeotropic removal of alcohol, especially aliphatic, cycloaliphatic and aromatic hydrocarbons or mixtures thereof.

Preference is given to n-pentane, n-hexane, n-heptane, cyclohexane, methylcyclohexane, benzene, toluene or xylene. Particular preference is given to cyclohexane, methylcyclohexane and toluene.

Very particular preference is given to not using a solvent in the transesterification and to using an excess of the lower (meth)acrylic ester used for the transesterification.

The transesterification may in general be carried out as follows:

The transesterification apparatus comprises for example a stirred reactor, preferably a reactor with circulatory evaporator and an added distillation unit.

The reactor may be for example a reactor with jacketed heating and/or internal heating coils. Preference is given to using a reactor having an external heat exchanger and natural or forced circulation, i.e., through use of a pump, more preferably natural circulation where circulation is accomplished without mechanical aids.

It will be appreciated that the reaction can also be carried out in a plurality of reaction zones, for example a reactor battery of two to four and preferably two or three reactors.

Suitable circulatory evaporators are known to one skilled in the art and are described for example in R. Billet, Verdampfertechnik, HTB-Verlag, Bibliographisches Institut Mannheim, 1965, 53. Examples of circulatory evaporators are tube-bundle heat exchangers, plate-type heat exchangers, etc.

It will be appreciated that the circulatory system may also include a plurality of heat exchangers.

The distillation unit is of conventional design. It may be a simple distillation unit which if appropriate is equipped with a splash guard or it may be a rectification column. Suitable column internals include in principle all common internals, for example trays, structured packings and/or dumped packings. Preferred trays include bubble-cap trays, sieve trays, valve trays. Thormann trays and/or dual-flow trays, while preferred dumped packings are those of rings, coils, saddles or braids.

In general, from 5 to 20 theoretical plates are sufficient.

The condenser is of conventional design.

The lower (meth)acrylic ester and the unsaturated amino alcohol are generally used in the transesterification in a molar excess as indicated above based on the hydroxyl groups of the alcohol. The excess used can be up to about 1000:1, if desired.

Useful transesterification catalysts include those recited above.

They are generally used in an amount from 0.1% to 5% by weight, based on the transesterification mixture, preferably in an amount from 0.5% to 5% by weight, more preferably in an amount from 1% to 4% by weight and most preferably in an amount from 2% to 4% by weight.

If necessary, the transesterification catalyst can be removed from the reaction mixture by means of an ion exchanger. If used, the ion exchanger can be added directly to the reaction mixture and subsequently filtered off or the reaction mixture can be passed through an ion exchanger bed.

However, when the catalyst is a suspended ion exchanger, it is preferably removed by filtration.

The polymerization inhibitor (mixture) is generally used in a total amount from 0.01 to 1% by weight, based on the transesterification mixture, preferably from 0.02 to 0.8% by weight, more preferably from 0.05 to 0.5% by weight.

The polymerization inhibitor (mixture) can be used for example as an alcoholic solution or as a solution in a reactant or product.

Stabilization may be further augmented by the presence of an oxygen-containing gas, preferably air or a mixture of air and nitrogen (lean air).

This oxygen-containing gas is preferably metered into a bottom region of a column and/or into a circulatory evaporator and/or passed through and/or over the reaction mixture.

The lower alcohol of reaction can be distilled off during or after the transesterification, in which case this operation can be augmented by a solvent which forms an azeotrope with the alcohol.

Using solvents for azeotropic removal of the alcohol, if desired, include the hydrocarbons recited above or the lower (meth)acrylic ester used in excess.

The transesterification is preferably carried out in the presence of an excess of lower (meth)acrylic ester.

When the lower alcohol in the reaction mixture is not removed via an azeotrope-forming solvent, it may be removed by stripping with an inert gas, preferably an oxygen-containing gas and more preferably air or lean air.

The reaction temperature for the transesterification is generally in the range from 40 to 160° C., preferably in the range from 60 to 140 C and more preferably in the range from 80 to 120° C. The temperature may remain constant or rise in the course of the reaction and preferably it is raised in the course of the reaction. In this case, the final temperature of the transesterification is 5-30° C. higher than the initial temperature. The temperature for the transesterification can be controlled by varying the solvent concentration in the reaction mixture or by varying the reaction pressure.

The distillate after condensation can be selectively removed and/or fed as a reflux into the distillation unit and/or be routed directly into the reaction zone and/or fed into a circulatory evaporator as described in WO 02/50014.

The reflux, as described in DE-A-199 41 136, may be used for controlling the temperature in the transesterification.

The transesterification can be carried out at atmospheric pressure, at superatmospheric pressure or at reduced pressure and is preferably carried out at atmospheric pressure or reduced pressure and more preferably at a reaction pressure in the range from 300 to 1 013 mbar.

The reaction time is generally in the range from 2 to 20 hours, preferably in the range from 4 to 15 and more preferably in the range from 7 to 12 hours.

The order in which the individual reaction components are added is not critical. All the components can be introduced as a mixed initial charge and subsequently heated, or one or more components can be omitted from or only partly included in the initial charge and added only after the initial charge has been heated up.

When the transesterification is carried out in a reactor equipped with a natural-circulation evaporator, it will be advantageous for the lower-boiling reaction components to be at least partly included in the initial charge.

The lower (meth)acrylic ester which can be used is not restricted in its composition and may, in the case of n-butyl acrylate, comprise for example the following components:

| | |
|---|---|
| n-butyl acrylate | 98-99.9% by weight |
| n-butyl acetate | 0.01-0.1% by weight |
| n-butyl propionate | 0.01-0.1% by weight |
| Water | 0.001-0.05 by weight |
| Carbonylics | 0.001-0.03% by weight |
| Acrylic acid | 0.001-0.01% by weight |
| Inhibitors | 0.001-0.002% by weight |

The (meth)acrylic ester used is generally stabilized with 10-20 ppm of hydroquinone monomethyl ether or other stabilizers in amounts which permit comparable stabilization. Carbonylics here refers for example to acetone and lower aldehydes, for example formaldehyde, acetaldehyde, crotonaldehyde, acrolein, 2-furfural, 3-furfural and benzaldehyde.

Circulation may be further supported by passing an inert gas, preferably an oxygen-containing gas, more preferably air or a mixture of air and nitrogen (lean air) into the circulatory evaporator from below, for example at rates of 0.1-1, preferably 0.2-0.8 and more preferably 0.3-0.7 $m^3/m^3h$, based on the volume of the reaction mixture.

The course of the transesterification can be monitored by monitoring the amount of alcohol carried out.

The reaction can be ended for example as soon as 90%, preferably at least 95% and more preferably at least 98% of the theoretically expected amount of alcohol has been carried out.

After the transesterification has ended, the transesterification catalyst is destroyed in a conventional manner. This is accomplished by addition of small amounts of water in the case of titanium alkoxides to form titanium dioxide precipitates which can be filtered off, or by neutralization, preferably with (meth)acrylic acid, in the case of alkali metal alkoxides.

In a further embodiment, the reaction mixture after the transesterification has ended may be diluted with water to a concentration of for example 10-90% by weight, preferably 20-80% by weight, more preferably 20-60% by weight, even more preferably 30-50% by weight and especially about 40% by weight, for example in order that the viscosity may be reduced.

If necessary, the reaction mixture may be decolorized, for example by treatment with activated carbon or metal oxides, for example alumina, silica, magnesium oxide, zirconium oxide, boron oxide or mixtures thereof, in amounts for example of 0.1-50% by weight, preferably from 0.5% to 25% by weight, more preferably 1-10% by weight at temperatures of for example from 10 to 100° C., preferably from 20 to 80° C. and more preferably from 30 to 60° C.

This can be effected by adding the pulverulent or granular decolorizing agent to the reaction mixture and subsequent filtration or by passing the reaction mixture through a bed of the decolorizing agent in the form of any desired suitable moldings.

The decolorizing of the reaction mixture can be effected at any desired stage in the workup process, for example at the stage of the crude reaction mixture or after any neutralization or after removal of the unreacted lower (meth)acrylic ester.

The lower (meth)acrylic ester used in excess for the transesterification and present in the reaction mixture can be substantially removed by distillation. Further low-boiling components present in the crude ester, solvents for example, are removed at the same time.

The distillative removal of the main amount of lower (meth)acrylic ester is effected for example in a stirred tank with jacketed heating and/or internal heating coils under reduced pressure, for example at 20-700 mbar, preferably 30-500 mbar and more preferably 50-150 mbar, and 40-120° C.

It will be appreciated that the distillation can also be accomplished in a falling-film or thin-film evaporator. For this, the reaction mixture is recirculated, preferably two or more times, through the apparatus under reduced pressure, for example at 20-700 mbar, preferably 30-500 mbar and more preferably 50-150 mbar, and 40-120° C.

When water is used as diluent, unconverted (meth)acrylic ester can be removed by azeotropic distillation. The distillate may, after condensation, be fed to a phase separation apparatus. The thus obtained organic phase may be removed from the system, while the aqueous phase can likewise be removed from the system or fed as a reflux into the distillation unit.

An inert gas, preferably an oxygen-containing gas, more preferably air or a mixture of air and nitrogen (lean air) may preferably be introduced into the distillation apparatus, for example 0.1-1 $m^3/m^3/h$, preferably 0.2-0.8 $m^3/m^3$ h and more preferably 0.3-0.7 $m^3/m^3/h$, based on the volume of the reaction mixture.

The level of starting ester in the residue after distillation is generally below 5% by weight, preferably in the range from 0.5 to 5% by weight and more preferably in the range from 1 to 3% by weight.

The removed (meth)acrylic ester may be condensed and preferably reused.

If necessary, a solvent stripping operation can be carried out in addition to or in lieu of the distillation.

For this, the target ester, which still contains small amounts of lower (meth)acrylic ester and/or solvent, is heated to 50-90° C. and preferably 80-90° C. and the remaining amounts of solvent are removed with a suitable gas in a suitable apparatus. A vacuum can be applied in support, if desired.

Examples of useful apparatus include columns of conventional design which contain conventional internals, for example trays, dumped packing or structural packing, preferably dumped packing. Useful column internals include in principle all common internals, for example trays, arranged packing and/or random packing. Preferred trays include bubble-cap trays, sieve trays, valve trays. Thormann trays and/or dual-flow trays, while preferred dumped packings are those of rings, coils, saddles, Raschig, Intos or Pall rings, barrel or Intralox saddles, Top-Pak, etc or braids.

Another possibility here is a falling-film, thin-film or wiped film evaporator, for example a Luwa, Rotafilm or Sambay evaporator, which may be splash-guarded with a demister for example.

Useful gases include gases which are inert under the stripping conditions, preferably oxygen-containing gases, more preferably air or mixtures of air and nitrogen (lean air) or water vapor, especially such gases which have been preheated to 50-100° C.

The stripping gas rate is for example in the range from 5 to 20, more preferably in the range from 10 to 20 and most preferably in the range from 10 to 15 $m^3/m^3h$, based on the volume of the reaction mixture.

If necessary, the (meth)acrylic ester of the unsaturated amino alcohol may at any stage of the workup process, but preferably after low-boilers removal has taken place, be subjected to a filtration in order that precipitated traces of salts and any decolorizing agent present may be removed.

The (meth)acrylic esters of unsaturated amino alcohols and inventive aqueous solutions obtainable by the above process may be used as free-radical crosslinker of water-absorbing hydrogels, as a starting material for producing polymer dispersions, as a starting material for producing polyacrylates (apart from hydrogels), as a paint raw material or as a cement additive.

Especially those inventive (meth)acrylic esters of unsaturated amino alcohols are useful as a free-radical crosslinker of water-absorbing hydrogels that have a solubility in distilled water at 25° C. of not less than 5% by weight, preferably not less than 10% by weight, more preferably not less than 20% by weight, even more preferably not less than 30% by weight and especially not less than 50% by weight.

Useful hydrophilic monomers for preparing the crosslinked swellable hydrogel-forming polymers include for example acids capable of addition polymerization, such as acrylic acid, methacrylic acid, ethacrylic acid, α-chloroacrylic acid, crotonic acid maleic acid, maleic anhydride, vinylsulfonic acid, vinylphosphonic acid, maleic acid, maleic anhydride, fumaric acid, itaconic acid, citraconic acid, mesaconic acid, glutaconic acid, aconitic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloyloxypropylsulfonic acid, allylphosphonic acid, styrenesulfonic acid, 2-acrylamido-2-methylpropanesulfonic acid, 2-acrylamido-2-methylpropanephosphonic acid and also their amides, hydroxyalkyl esters and amino- or ammonio-containing esters and amides. These monomers can be used alone or mixed with each other. Furthermore water-soluble N-vinylamides and also diallyldimethylammonium chloride.

Particularly preferred hydrophilic monomers are acrylic acid and methacrylic acid.

To optimize properties, it can be sensible to use additional monoethylenically unsaturated compounds which do not bear an acid group but are copolymerizable with the monomers bearing acid groups. Such compounds include for example the amides and nitriles of monoethylenically unsaturated carboxylic acids, for example acrylamide, methacrylamide and N-vinylformamide, N-vinylacetamide, N-methylvinylacetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least two carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_8$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses ($M_n$) of the polyalkylene glycols being up to 2 000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

The crosslinked (co)polymers preferably consist of acid-functional monoethylenically unsaturated monomers which have optionally been converted into their alkali metal or ammonium salts before or after polymerization and of 0-40% by weight based on their total weight of monoethylenically unsaturated monomers which do not bear acid groups.

The production of (meth)acrylic acid (co)polymers, polyacrylic acids and superabsorbents has been extensively described before, see for example "Modern Superabsorbent Polymer Technology", F. L. Buchholz and A. T. Graham, Wiley-VCH, 1998, pages 69 to 117.

Preference is given to such hydrogels which are obtained by crosslinking addition polymerization or copolymerization of acid-functional monoethylenically unsaturated monomers or salts thereof.

In the postcrosslinking process, the starting polymer is treated with a postcrosslinker and preferably during or after the treatment postcrosslinked and dried by raising the temperature, the crosslinker preferably being included in an inert solvent. Inert solvents are solvents which substantially do not react either with the starting polymer or with the postcrosslinker. Preference is given to such solvents which do not react chemically with the starting polymer or with the postcrosslinker to an extent of more than 90%, preferably more than 95%, more preferably more than 99% an especially more than 99.5%.

Postcrosslinking and drying is preferably carried out at from 30 to 250° C., especially 50-200° C. and most preferably at from 100 to 180° C. The surface postcrosslinking solution is preferably applied by spraying the polymer in suitable spray mixers. After spraying, the polymer powder is thermally dried, and the crosslinking reaction can take place not only before but also during the drying operation. Preference is given to spraying a solution of the crosslinker in reaction mixers or mixing and drying ranges such as for example Lödige mixers, BEPEX mixers, NAUTA mixers, SHUGGI mixers or PROCESSALL. It is moreover also possible to use fluidized bed dryers.

The drying operation can take place in the mixer itself, by heating of the shell or by blowing in hot air. Also suitable is a downstream dryer such as for example a shelf dryer, a rotary tube oven or a heatable screw. But it is also possible to utilize an azeotropic distillation as drying technique, for example. The preferred residence time at this temperature in the reaction mixer or dryer is below 60 min and more preferably below 30 min.

Preference is given to the above processes wherein the starting polymer is a polymeric (meth)acrylic acid or a poly (meth)acrylate, especially a polymeric acrylic acid or a polyacrylate obtained by free-radical polymerization using a polyfunctional ethylenically unsaturated free-radical crosslinker.

Preference is given to such processes wherein the free-radical crosslinker is used in a dose of 0.01-5.0% by weight, preferably 0.02-3.0% by weight, more preferably 0.03-2.5% by weight, especially 0.05-1.0% and specifically from 0.1% to 0.75% by weight based on the starting polymer.

The present invention also provides polymers prepared by one of the processes mentioned above and for their use in hygiene articles, packaging materials and nonwovens and also for the use of an abovementioned composition of matter for producing crosslinking or thermally crosslinkable polymers, especially in paints and varnishes.

The crosslinked swellable hydrogel-forming polymers to be used (starting polymers) are in particular polymers of (co)polymerized hydrophilic monomers, graft (co)polymers of one or more hydrophilic monomers on a suitable grafting base, crosslinked cellulose or starch ethers or natural products capable of swelling in aqueous fluids, for example guar derivatives. These hydrogels are known to one skilled in the art and are described for example in U.S. Pat. No. 428,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A-26 12 846, DE-A-40 20 780 EP-A-0 205 674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497. Also of particularly suitability are crosslinked swellable hydrogel-forming polymers from a manufacturing operation as described in WO 01/38402 and also crosslinked swellable inorganic/organic hybrid hydrogel-forming polymers as described in DE 198 54 575. The content of the aforementioned patent documents, especially the hydrogels produced by the processes, is explicitly incorporated herein by reference.

Suitable grafting bases for crosslinked swellable hydrogel-forming polymers obtainable by graft copolymerization of olefinically unsaturated acids can be of natural or synthetic origin. Examples are starch, cellulose, cellulose derivatives and also other polysaccharides and oligosaccharides, polyalkylene oxides, especially polyethylene oxides and polypropylene oxides, and also hydrophilic polyesters.

The crosslinked swellable hydrogel-forming polymer is obtainable by free-radical graft copolymerization of acrylic acid or acrylate onto a water-soluble polymer matrix. Non-limiting examples of suitable water-soluble polymer matrices are alginates, polyvinyl alcohol and polysaccharides such as starch for example. A graft copolymerization for the purposes of the present invention utilizes a polyfunctional ethylenically unsaturated free-radical crosslinker.

The crosslinked swellable hydrogel-forming polymer can be organic/inorganic hybrid polymer formed from a polymeric acrylic acid or polyacrylate on the one hand and a silicate, aluminate or aluminosilicate on the other. More particularly, the polymeric acrylic acid or polyacrylate used may have been obtained by free-radical polymerization using a polyfunctional ethylenically unsaturated free-radical crosslinker and formed using a water-soluble silicate or soluble aluminate or mixture thereof.

Preferred crosslinked swellable hydrogel-forming polymers are in particular polyacrylates, polymethacrylates and also the graft polymers described in U.S. Pat. No. 4,931,497, U.S. Pat. No. 5,011,892 and U.S. Pat. No. 5,041,496. Very particularly preferred crosslinked swellable hydrogel-forming polymers are the kneader polymers described in WO 01/38402 and the polyacrylate-based crosslinked swellable organic/inorganic hybrid hydrogel-forming polymers described in DE 198 545 75.

The substances prepared according to the present invention, which are useful as free-radical crosslinkers in crosslinked swellable hydrogel-forming polymers, can be used alone or in combination with other crosslinkers, for example internal or surface crosslinkers, for example the following:

Methylenebisacrylamide, methylenebismethacrylamide, esters of unsaturated mono- or polycarboxylic acids with polyols, such as diacrylate or triacrylate, for example butanediol diacrylate, butanediol dimethacrylate, ethylene glycol diacrylate, ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Further suitable cocrosslinkers are pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated variants thereof. Particularly preferred cocrosslinkers further include polyethylene glycol diacrylates, ethoxylated derivatives of trimethylolpropane triacrylate, for example Sartomer® SR 9035, and also ethoxylated derivatives of glycerol diacrylate and glycerol triacylate. It is obviously also possible to use mixtures of the above crosslinkers.

Very particular preference is given to those crosslinked swellable hydrogel-forming polymers which are prepared using an inventively prepared methacrylic ester of an unsaturated amino alcohol as sole free-radical crosslinker.

The crosslinked swellable hydrogen-forming polymer is preferably a polymeric acrylic acid or a polyacrylate.

The crosslinked swellable hydrogen-forming polymers are preparable by addition polymerization processes known per se. Preference is given to the addition polymerization in aqueous solution conducted as a gel polymerization. It involves, as stated above, dilute, preferably aqueous and more preferably 15-50% by weight aqueous, solutions of one or more hydrophilic monomers and optionally of a suitable grafting base being polymerized in the presence of a free-radical initiator by utilizing the Trommsdorff-Norrish effect (Makromol. Chem. 1, 169 (1947)) preferably without mechanical mixing. The polymerization reaction may be carried out at from 0° C. to 150° C., and preferably at from 10° C. to 100° C., not only at atmospheric pressure but also at superatmospheric or reduced pressure. Typically, the polymerization can also be carried out in a protective gas atmosphere, preferably under nitrogen. The addition polymerization may be induced using high-energy electromagnetic rays or the customary chemical polymerization initiators, for example organic peroxides, such as benzoyl peroxide, tert-butyl hydroperoxide, methyl ethyl ketone peroxide, cumene hydroperoxide, azo compounds such as azobisisobutyronitrile and also inorganic peroxy compounds such as $(NH_4)_2S_2O_8$, $K_2S_2O_8$ or $H_2O_2$.

They can if desired be used in combination with reducing agents such as ascorbic acid, sodium hydrogensulfite and iron(II) sulfate or redox systems where the reducing component included is an aliphatic and aromatic sulfinic acid, such as benzenesulfinic acid and toluenesulfinic acid or derivatives thereof, for example Mannich adducts of sulfinic acids, aldehydes and amino compounds, as described in DE-C-1 301 566. The performance properties of the polymers can be further improved by postheating the polymer gels in the temperature range from 50° C. to 130° C. and preferably from 70° C. to 100° C. for several hours.

The gels obtained are neutralized to the extent of 0-100 mol %, preferably 25-100 mol % and more preferably 50-85 mol % based on monomer used, for which the customary neutralizing agents can be used, preferably alkali metal hydroxides, alkali metal oxides or the corresponding alkali metal carbonates, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization.

The neutralization gel mass is then dried with a belt or can dryer until the residual moisture content is preferably below 10% by weight and especially below 5% by weight.

The addition polymerization as such can also be carried out by any other process described in the literature. More particularly, the neutralization of the acrylic acid can also be carried out prior to the polymerization, as described above. The polymerization can then be carried out in a conventional belt reactor or a kneading reactor continuously or else batchwise. When the polymerization is carried out in a belt reactor, initiation by electromagnetic radiation and preferably by UV radiation or alternatively initiation by means of a redox initiator system is particularly preferred. Very particular preference is also given to a combination of the two methods of initiation: electromagnetic radiation and chemical redox initiator system simultaneously.

The dried crosslinked swellable hydrogel-forming polymer can then be ground and sieved, in which case it is customary to use roll mills, pin mills or vibratory mills for the grinding. The preferred particle size of the sieved hydrogel is preferably in the range 45-1 000 µm, more preferably at 45-850 µm, even more preferably at 100-800 µm, and most preferably at 100-700 µm. These ranges preferably cover 80% by weight of the particles and especially 90% by weight of the particles. The size distribution can be determined using established laser methods.

The present invention further provides crosslinked swellable hydrogel-forming polymers which contain at least one hydrophilic monomer in polymerized form and are crosslinked with a (meth)acrylic ester of an unsubstituted amino alcohol of the formula (I).

Preferred (meth)acrylic esters of unsaturated amino alcohols are those of the formula (I), as defined above, in each of which q is independently for p-2 a number from 1 to 100, preferably from 3 to 30, more preferably from 5 to 15 and for p=1 a number from 1 to 100, preferably from 5 to 40, more preferably from 8 to 20.

The unsaturated amino alcohols which are described by the formula (II) and whose (meth)acrylic esters are used as a crosslinker in the aforementioned crosslinked swellable hydrogel-forming polymers are each alkoxylated, preferably ethyoxylated, propoxylated or mixedly ethoxylated and propoxylated and especially ethoxylated or mixedly ethoxylated and propoxylated and most preferably exclusively ethoxylated.

Particularly preferred (meth)acrylic esters of unsaturated amino alcohols are those of the formula (I) whose unsaturated amino alcohols are derived from diallylamine, allylamine and allylmethylamine.

The CRC value [g/g] of the inventive crosslinked swellable hydrogel-forming polymers may be measured by the methods indicated in the description and is at least 9, preferably above 15, especially above 20, more preferably above 25, especially above 30, more preferably above 35.

The AUL 0.7 psi value [g/g] of the inventive crosslinked swellable hydrogel-forming polymers may be measured by the methods indicated in the description and is after post-crosslinking preferably above 5, especially above 10, more preferably above 15, especially above 20 and even more preferably 25.

The present invention further relates to the use of the abovementioned hydrogel-forming polymers in hygiene articles comprising (A) a liquid-pervious topsheet
(B) a liquid-impervious backsheet
(C) a core positioned between (P) and (Q) and comprising
    10-100% by weight of the crosslinked swellable hydrogel-forming polymer according to the present invention
    0-90% by weight of hydrophilic fiber material
    preferably 30-100% by weight of the crosslinked swellable hydrogel-forming polymer according to the present invention, 0-70% by weight of hydrophilic fiber material
    more preferably 50-100% by weight of the crosslinked swellable hydrogel-forming polymer according to the present invention, 0-50% by weight of hydrophilic fiber material
    especially preferably 70-100% by weight of the crosslinked swellable hydrogel-forming polymer according to the present invention, 0-30% by weight of hydrophilic fiber material
    most preferably 90-100% by weight of the crosslinked swellable hydrogel-forming polymer according to the present invention, 0-10% by weight of hydrophilic fiber material
(D) optionally a tissue layer positioned directly above and below said core (C), and
(E) optionally an acquisition layer positioned between (A) and (C).

Hygiene articles for the purposes of the present invention include, for example, not only incontinence pads and incontinence briefs for adults but also diapers for infants.

The liquid-pervious topsheet (A) is the layer which is in direct contact with the skin. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon and blends thereof, polyethylene and polypropylene. Examples of liquid-pervious layers are described in WO 99/57355, EP-A-1 023 883.

The liquid-impervious layer (B) is generally a sheet of polyethylene or polypropylene.

The core (C) includes not only the crosslinked swellable hydrogel-forming polymer according to the present invention but also hydrophilic fiber material. By hydrophilic is meant that aqueous fluids spread quickly over the fiber. The fiber material is usually cellulose, modified cellulose, rayon, polyester such s polyethylene terephthalate. Particular preference is given to cellulose fibers such as pulp. The fibers generally have a diameter of 1-200 µm and preferably 10-100 µm, and also have a minimum length of 1 mm.

Diaper construction and shape is common knowledge and described for example in WO 95/26209 page 66 line 34 to page 69 line 11, DE-A-196 04 601, EP-A-0 316 518 and EP-A-0 202 127. Diapers and other hygiene articles are generally also described in WO 00/65084, especially at pages 6-15, WO 00/65348, especially at pages 4-17, WO 00/35502, especially pages 3-9, DE-A 197 37 434 and WO 98/08439. Hygiene articles for feminine care are described in the following references. The inventive crosslinked swellable hydrogel-forming polymers capable of absorbing aqueous fluids can be used there. Feminine care references: WO 95/24173: Absorption Article for Controlling Odour, WO 91/11977: Body Fluid Odour Control, EP-A-0 389 023: Absorbent Sanitary Articles, WO 94/25077: Odour Control Material, WO 97/01317: Absorbent Hygienic Article, WO 99/18905, EP-A-0 834 297, U.S. Pat. No. 5,762,644, U.S. Pat. No. 5,895,381, WO 98/57609, WO 00/65083, WO 00/69485, WO 00/69484, WO 00/69481, U.S. Pat. No. 6,123,693, EP-A-1 104 666, WO 01/24755, WO 01/00115, EP-A-0 105 373, WO 01/41692, EP-A-1 074 233. Tampons are described in the following references: WO 98/48753, WO 98/41179, WO 97/09022, WO 98/46182, WO 98/46181, WO 01/43679, WO 01/43680, WO 00/61052, EP-A-1 108 408, WO 01/33962, DE-A-100 20 662, WO 01/01910, WO 01/01908, WO 01/01909, WO-01/01906, WO 01/01905, WO 01/24729. Incontinence articles are described in the following references: Disposable Absorbent Article for Incontinent Individuals: EP-A-0 311 344 description pages 3-9; Disposable Absorbent Article: EP-A-0 850 623, Absorbent Article: WO 95/26207, Absorbent Article: EP-A-0 894 502, Dry Laid Fibrous Structure: EP-A-0 850 616, WO 98/22063, WO 97/49365, EP-A-0 903 134, EP-A-0 887 060, EP-A-0 887 059, EP-A-0 887 058, EP-A-0 887 057, EP-A-0 887 056, EP-A-0 931 530, WO 99/25284, WO 98/48753. Feminine care and incontinence articles are described in the following references: Catamenial Device: WO 93/22998 description pages 26-33; Absorbent Members for Body Fluids: WO 95/26209 description pages 36-69; Disposable Absorbent Article: WO 98/20916 description pages 13-24; Improved Composite Absorbent Structures: EP-A-0 306 262 description pages 3-14; Body Waste Absorbent Article: WO 99/45973. These references are hereby expressly incorporated herein.

The crosslinked swellable hydrogel-forming polymers according to the present invention are very useful as absorbents for water and aqueous fluids, so that they may be used with advantage as a water retainer in market gardening, as a filter aid and particularly as an absorbent component in hygiene articles such as diapers, tampons or sanitary napkins.

In addition to the above-described crosslinked swellable hydrogel-forming polymers, the absorbent composition of the present invention includes constructions which include crosslinked swellable hydrogel-forming polymers or to which they are fixed. Any construction is suitable that is capable of accommodating crosslinked swellable hydrogel-forming polymers and also of being integrated into the absorption layer. A multiplicity of such compositions is already known. A construction for installing the crosslinked swellable hydrogel-forming polymers can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28478. Furthermore, open-celled foams or the like may be used to install crosslinked swellable hydrogel-forming polymers.

Alternatively, such a construction can be the result of fusing two individual layers to form one or better a multiplicity of chambers which contain the crosslinked swellable hydrogel-forming polymers. Such a chamber system is described in detail in EP-A-0 615 736 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the crosslinked swellable hydrogel-forming polymer particles. The above examples of the construction of the absorbent composition also include laminates composed of at least two layers between which the crosslinked swellable hydrogel-forming polymers are installed and fixed.

Generally it is possible to fix hydrogel particles within the absorbent core to improve dry and wet integrity. Dry and wet integrity describes the ability to install crosslinked swellable hydrogel-forming polymers into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26209 page 37 line 36 to page 41 line 14. The cited passage is thus part of this invention. Methods for enhancing wet strength are also to be found in WO 00/36216.

Furthermore, the absorbent composition may comprise a base material, for example a polymer film on which the crosslinked swellable hydrogel-forming polymer particles are fixed. The fixing may be effected not only on one side but also on both sides. The base material can be water pervious or water impervious.

The above constructions of the absorbent composition incorporate the crosslinked swellable hydrogel-forming polymers at a weight fraction of from 10-100% by weight, preferably 30-100% by weight, more preferably 50-100% by weight, especially preferably 70-100% by weight, and most preferably 90-100% by weight, based on the total weight of the construction and of the crosslinked swellable hydrogel-forming polymers.

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluorethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylenebicomponent fibers, polyester fibers, such as polyethylene terephthalate fibers (DACRON® or KODEL®), copolyester, polyvinyl acetate, polyethyl vinyl acetate, polyvinyl chloride, polyvinylidene chloride, polyacrylics, polyamides, copolyamides, polystyreneo and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyeser/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent layer, to continuously increase the fraction of thermoplastic fibers in the direction of the topsheet, which results in a similarly continuous increase of the pore sizes. Thermoplastic fibers can be formed from a multiplicity of thermoplastic polymers which have a melting point of less than 190° C., preferably in the range from 76° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9 000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the present invention can be hydrophilic and/or hydrophobic. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the crosslinked swellable hydrogel-forming polymers. In the manufacturing process, layers having different hydrophilicities are used to create a gradient which channels impinging fluid to the hydrogel, where it is ultimately absorbed.

Suitable hydrophilic fibers for use in the absorbent composition of the present invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophlicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and reasons of availability, cellulosic fibers are preferred.

The crosslinked swellable hydrogel-forming polymer particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557H, Hercules, Inc. Wilmington Del., USA), polyacrylamide coatings (described in U.S. Pat. No. 3,556,932 or as the Parez® 631 NC commercial product from American Cyanamid Co., Stamford, Conn., USA), melamine-Formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$-$C_8$-dialdehydes, $C_2$-$C_8$-monoaldehydes having acid functionality and in particular $C_2$-$C_9$-polycarboxylic acids. Specific substances from this series are for example glutaraldehyde, glyoxal, glyoxylic acid, formaldehyde and citric acid. These substances react with at least two hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. No. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Examples of processes to obtain an absorbent composition comprising for example a base material to which crosslinked swellable hydrogel-forming polymers are fixed on one or both sides are known and included by the invention but not limited thereto.

Examples of processes to obtain an absorbent composition comprising for example a fiber material blend of synthetic fibers (a) and cellulose fibers (b) embedded in crosslinked swellable hydrogel-forming polymers (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., more preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26209.

The present invention further provides hygiene articles comprising crosslinked swellable hydrogen-forming polymers which contain at least one hydrophilic monomer in polymerized form and are crosslinked with a (meth)acrylic ester of an unsaturated amino alcohol of the formula (I).

The examples which follow illustrate the process of the present invention.

EXAMPLES

Measurement Methods

Centrifuge Retention Capacity (CRC)

This method measures the free swellability of the hydrogel in a teabag. 0.2000±0.0050 g of dried hydrogel (particle size fraction 106-850 μm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 G. The amount of liquid retained by the hydrogel is determined by weighing back the centrifuged teabag.

Extractions

The 16 h extractables value is determined similarly to the description in EP-A-0 811 636 at page 13 line 1 to line 19.

Preparation of Allylamine Polyethers

Example 1

Diallylamine-5 EO 97 g of diallylamine are placed with 0.5 g of KOH, 45% in water, as an initial charge in an autoclave, which is purged with argon, and are then dewatered together at 80 C and reduced pressure (about 20 mbar). 220 g of ethylene oxide are then added at 145 to 155° C. and allowed to react at this temperature under elevated pressure. The reaction has ended when no further change in pressure is observed. The reaction mixture is then stirred for a further 30 min at 120° C. After purging with inert gas and cooling to 60° C., the catalyst is separated off by addition of sodium pyrophosphate and subsequent filtration.

Example 2

Diallylamine-13 EO

Example 1 is repeated except that the 97 g of diallylamine are initially admixed with 44 g of ethylene oxide, then cooled down to room temperature and admixed with 0.5 g of KOH, 45% in water. This produces, in known manner, initially the diallylamine 1 EO, which is further ethoxylated hereinbelow similarly to Example 1.

The autoclave is purged with argon, and the reaction mixture is then dewatered at 80° C. and reduced pressure (about 20 mbar). A further 528 g of ethylene oxide are then added at 145 to 155° C. and allowed to react at this temperature under elevated pressure. The reaction has ended when no further change in pressure is observed. The reaction mixture is then stirred for a further 30 min at 120° C. After purging with inert gas and cooling to 60° C., the catalyst is separated off by addition of sodium pyrophosphate and subsequent filtration.

Example 3

Diallylamine-18 EO

Example 1 is repeated except that the 97 g of diallylamine are admixed with 792 g of ethylene oxide as well as 0.5 g of KOH.

Example 4

Monoallylamine-5 EO 57 g of monoallylamine are placed with 0.5 g of KOH, 56% in water, as an initial charge in an autoclave, which is purged with argon, and are then dewatered together at 80° C. and reduced pressure (about 20 mbar). 220 g of ethylene oxide are then added at 145 to 155° C. and allowed to react at this temperature under elevated pressure. The reaction has ended when no further change in pressure is observed. The reaction mixture is then stirred for a further 30 min at 120° C. After purging with inert gas and cooling to 60° C., the catalyst is separated off by addition of sodium pyrophosphate and subsequent filtration.

Example 5

Monoallylamine 13 EO

Example 4 is repeated except that the 57 g of monoallylamine are admixed with 572 g of ethylene oxide as well as 0.5 g of KOH.

Preparation of Ethoxylated Acrylate-Allylamines

Example 6

Diallylamine-5 EO-monoacrylate 80 g of the 5-tuply ethoxylated diallylamine of Example 1 are introduced as an initial charge with 215 g of methyl acrylate, 10 g of Novozym (immobilized lipase from Candida antartica) and 0.4 g of hydroquinone monomethyl ether and esterified at 60° C. by transesterification. The methanol formed is continuously distilled off at 500-560 mbar, and a portion of the methyl acrylate used passes over as well. After about 8 hours methyl acrylate as needed and a further 10 g of Novozym are added and the esterification is continued for 8 hours. The crude product is separated from the Novozym catalyst by filtration and subsequently the excess methyl acrylate is distilled out of the product in a rotary evaporator.

Examples 7 to 10

Example 6 is repeated with the use levels reported in Table 1.

Comparative Example 2

Tripropylene Glycol Diacrylate

A Lödige VT 5R-MK plowshare kneader (5 l volume) is charged with 388 g of deionized water, 173.5 g of acrylic acid, 2033.2 g of a 37.3% by weight sodium acrylate solution (100 mol % neutralized) and also 2.10 g of the crosslinker tripropylene glycol diacrylate (Laromer® TPGDA, from BASF AG). This initial charge is inertized having nitrogen bubbled through it for 20 minutes. Dilute aqueous solutions of 2.112 g of sodium persulfate, 0.045 g of ascorbic acid and also 0.126 g of hydrogen peroxide are then added to start the reaction at about 23° C. After the reaction has started, the temperature of the heating jacket is controlled to the reaction temperature in the reactor. The crumbly gel eventually obtained is then dried in a circulating air drying cabinet at 160 C for about 3 h. This is followed by grinding and classifying to 300-600 micrometers. The hydrogel obtained is then surface postcrosslinked.

TABLE 1

| Example | Allylamine polyether | Methyl Acrylate* | Novozym* | Hydroquinone monomethyl ether | Vitamin E** |
|---|---|---|---|---|---|
| 7 | 84 g diallylamine - 13 EO from Example 2 | 108 g | 10 g | 0.3 g | 0.2 g |
| 8 | 111 g diallylamine - 18 EO from Example 3 | 108 g | 10 g | 0.3 g | 0.3 g |
| 9 | 70 g monoallylamine - 5 EO from Example 4 | 216 g | 10 g | — | 0.5 g |
| 10 | 79 g monoallylamine - 13 EO from Example 5 | 108 g | 10 g | 0.4 g | 0.2 g |

*use level at start of batch; after 8 hours, further methylacrylate and Novozym were added as needed similarly to Example 6
**Vitamin E is introduced as an initial charge together with hydroquinone monomethyl ether Illustrative Production of Superabsorbents:

Comparative Example 1

Trimethylolpropane-15 EO-triacrylate

A Lödige VT 5R-MK plowshare kneader (5 l volume) is charged with 388 g of deionized water, 173.5 g of acrylic acid, 2033.2 g of a 37.3% by weight sodium acrylate solution (100 mol % neutralized) and also 4.50 g of the crosslinker trimethylolpropane-15 EO-triacrylate (Sartomer®) SR 9035, from Sartomer). This initial charge is inertized having nitrogen bubbled through it for 20 minutes. Dilute aqueous solutions of 2.112 g of sodium persulfate, 0.045 g of ascorbic acid and also 0.126 g of hydrogen peroxide are then added to start the reaction at about 23° C. After the reaction has started, the temperature of the heating jacket is controlled to the reaction temperature in the reactor. The crumbly gel eventually obtained is then dried in a circulating air drying cabinet at 160° C. for about 3 h. This is followed by grinding and classifying to 300-600 micrometers. The hydrogen obtained is then surface postcrosslinked. The properties of the hydrogel obtained are summarized in the table which follows.

The properties of the hydrogel obtained are summarized in the table which follows.

Examples 11 to 15

Comparative Example 1 is repeated using the crosslinkers reported in Table 2 in the amounts reported therein.

TABLE 2

| | Crosslinker | Amount used | CRC [g/g] | Extract. 16 h [wt. %] |
|---|---|---|---|---|
| Comparative Example 1 | Sartomer ® SR 9035 | 4.5 g | 35 | 10% |
| Comparative Example 2 | Laromer ® TPGDA | 2.1 g | 41 | 19% |
| Example 11 | from Example 6 | 1.7 g | 36 | 8% |
| Example 12 | from Example 7 | 3.4 g | 37 | 8% |
| Example 13 | from Example 8 | 4.4 g | 35 | 6% |
| Example 14 | from Example 9 | 1.8 g | 37 | 5% |
| Example 15 | from Example 10 | 3.5 g | 36 | 7% |

The amounts used are computed such that in each case there is the same number of double bond equivalents based on acrylic acid monomer for crosslinking. It can be seen that the crosslinkers used according to the present invention each combine a somewhat higher CRC value with a distinctly lower extractables content. Such behavior in advantageous in that extractables have an adverse effect on product properties.

We claim:

1. (Meth)acrylic esters of unsaturated aminoalcohols of general formula (I)

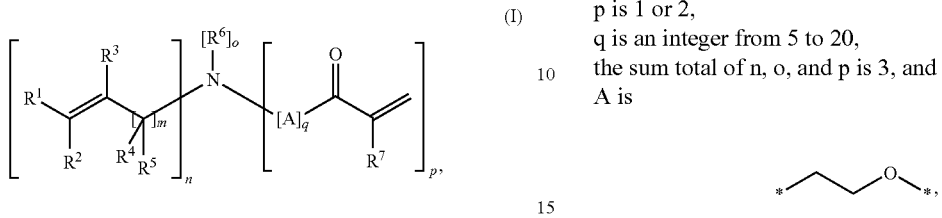

wherein
- $R^1$, $R^2$, $R^3$, $R^4$, and $R^5$ are each independently hydrogen or $C_1$ to $C_6$ alkyl, of which $C_3$ to $C_6$ alkyl may be branched or unbranched,
- $R^6$ is $C_1$ to $C_6$ alkyl, of which $C_3$ to $C_6$ alkyl may be branched or unbranched,
- $R^7$ is hydrogen or methyl,
- m is an integer from 0 to 10,
- n is 1 or 2,
- o is 0 or 1,
- p is 1 or 2,
- q is an integer from 2 to 100,
- the sum total of n, o, and p is 3, and
- A represents identical or different radicals selected from the group consisting of

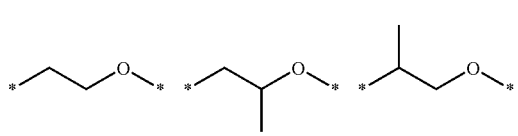

wherein * identifies the positions of attachment.

2. (Meth)acrylic esters of claim 1 wherein
- $R^1$, $R^2$, $R^3$, $R^4$, and $R^5$ are each hydrogen,
- $R^6$ is $C_1$ to $C_3$ alkyl, of which $C_3$ alkyl may be branched or unbranched,
- $R^7$ is hydrogen or methyl,
- m is 0 or 1,
- n is 1 or 2,
- o is 0 or 1,
- p is 1 or 2,
- q is an integer from 3 to 40,
- the sum total of n, o, and p is 3, and
- A represents identical or different radicals selected from the group consisting of

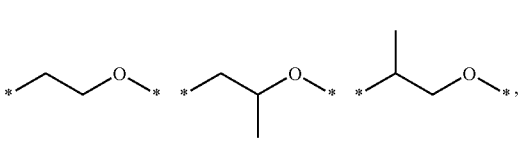

wherein * identifies the positions of attachment.

3. (Meth)acrylic esters of claim 1 wherein
- $R^1$, $R^2$, $R^3$, $R^4$, and $R^5$ are each hydrogen,
- $R^7$ is hydrogen or methyl,
- m is 1,
- n is 1 or 2,
- o is 0,
- p is 1 or 2,
- q is an integer from 5 to 20,
- the sum total of n, o, and p is 3, and
- A is

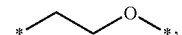

wherein * identifies the positions of attachment.

4. A process for preparing the (meth)acrylic esters of claim 1 comprising unsaturated aminoalcohols being transesterified with lower (meth)acrylic esters in the presence of a catalyst, a released lower alcohol being distilled off during the transesterification, optionally as an azeotrope, and unconverted lower (meth)acrylic ester being distilled off after the transesterification has ended, optionally diluted with water and filtered.

5. A swellable hydrogel-forming polymer comprising a copolymerized internal crosslinker of a general formula (I)

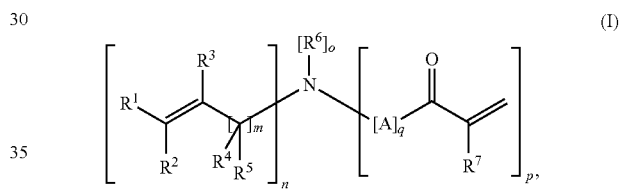

wherein
- $R^1$, $R^2$, $R^3$, $R^4$, and $R^5$ are each independently hydrogen or $C_1$ to $C_6$ alkyl, of which $C_3$ to $C_6$ alkyl may be branched or unbranched,
- $R^6$ is $C_1$ to $C_6$ alkyl, of which $C_3$ to $C_6$ alkyl may be branched or unbranched,
- $R^7$ is hydrogen or methyl,
- m is an integer from 0 to 10,
- n is 1 or 2,
- o is 0 or 1,
- p is 1 or 2,
- q is an integer from 1 to 100,
- the sum total of n, o, and p is 3, and
- A represents identical or different radicals selected from the group consisting of

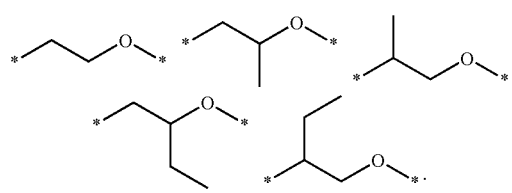

6. A swellable hydrogel-forming polymer comprising a copolymerized (meth)acrylic ester of an unsaturated aminoalcohol of claim 2 as an internal crosslinker.

7. A swellable hydrogel-forming polymer comprising a copolymerized (meth)acrylic ester of an unsaturated aminoalcohol of claim 3 as an internal crosslinker.

8. A process for preparing crosslinked swellable hydrogel-forming polymers of claim 5 which comprises polymerizing an aqueous mixture comprising a hydrophilic monomer, optionally at least one further monoethylenically unsaturated compound, at least one (meth)acrylic ester of unsaturated aminoalcohols, at least one free-radical initiator, optionally at least one grafting base, and optionally a reaction mixture obtained being postcrosslinked, dried, and brought to the desired particle size.

9. A hygiene article comprising a crosslinked swellable hydrogel-forming polymer of claim 5.

10. A process for preparing crosslinked swellable hydrogel-forming polymers of claim 6 which comprises polymerizing an aqueous mixture comprising a hydrophilic monomer, optionally at least one further monoethylenically unsaturated compound, at least one (meth)acrylic ester of unsaturated aminoalcohols, at least one free-radical initiator, optionally at least one grafting base, and optionally a reaction mixture obtained being post-crosslinked, dried, and brought to the desired particle size.

11. A process for preparing crosslinked swellable hydrogel-forming polymers of claim 7 which comprises polymerizing an aqueous mixture comprising a hydrophilic monomer, optionally at least one further monoethylenically unsaturated compound, at least one (meth)acrylic ester of unsaturated amino alcohols, at least one free-radical initiator, optionally at least one grafting base, and optionally a reaction mixture obtained being post-crosslinked, dried, and brought to the desired particle size.

12. The swellable hydrogel-forming polymer of claim 5 wherein the internal crosslinker of general formula (I) according to claim 1 is copolymerized with an acid functional monoethylenically unsaturated monomer, a salt thereof, or mixtures thereof.

13. The swellable hydrogel-forming polymer of claim 12 wherein the acid functional monoethylenically unsaturated monomer comprises acrylic acid, methacrylic acid, a salt thereof, or mixtures thereof.

14. The swellable hydrogel-forming polymer of claim 6 wherein the internal crosslinker according to claim 2 is copolymerized with an acid functional monoethylenically unsaturated monomer, a salt thereof, or mixtures thereof.

15. The swellable hydrogel-forming polymer of claim 14 wherein the acid functional monoethylenically unsaturated monomer comprises acrylic acid, methacrylic acid, a salt thereof, or mixtures thereof.

16. The swellable hydrogel-forming polymer of claim 7 wherein the internal crosslinker according to claim 3 is copolymerized with an acid functional monoethylenically unsaturated monomer, a salt thereof, or mixtures thereof.

17. The swellable hydrogel-forming polymer of claim 16 wherein the acid functional monoethylenically unsaturated monomer comprises acrylic acid, methacrylic acid, a salt thereof, or mixtures thereof.

* * * * *